United States Patent [19]
Walters

[11] 4,023,095
[45] May 10, 1977

[54] CIRCUIT FOR MEASURING THE SENSITIVITY OF A CARDIAC PACER

[75] Inventor: Robert A. Walters, Pittsburgh, Pa.

[73] Assignee: ARCO Medical Products Company, Leechburg, Pa.

[22] Filed: Mar. 15, 1976

[21] Appl. No.: 666,739

[52] U.S. Cl. .............................. 324/57 R; 324/63
[51] Int. Cl.² ........................................ G01R 27/00
[58] Field of Search ............................ 324/57 R, 63

[56] References Cited
UNITED STATES PATENTS

| | | | |
|---|---|---|---|
| 3,566,286 | 2/1971 | Freeman | 324/57 R X |
| 3,676,774 | 7/1972 | Stokes et al. | 324/63 X |
| 3,927,368 | 12/1975 | Zielonko et al. | 324/57 R |

Primary Examiner—Stanley T. Krawczewicz
Attorney, Agent, or Firm—Richard A. Bachand

[57] ABSTRACT

A circuit for measuring the sensitivity of a cardiac pacer includes a generator for producing a signal which varies as a function of the sine² of a predetermined frequency. The signal is generated by an intermediate step of generating a waveform having the value of ½ [1−COS($\theta$/2)]. The waveform is applied to an input of a cardiac pacer, and the amplitude varied in a measurable manner. The output of the cardiac pacer is observed in response to the signals applied to its input, and the amplitude of the voltage waveform which just inhibits the operation of the pacer is directly read from the amplitude varying control.

5 Claims, 1 Drawing Figure

CIRCUIT FOR MEASURING THE SENSITIVITY OF A CARDIAC PACER

BACKGROUND OF THE INVENTION

1. Field of the Invention

This invention relates to improvements in circuits for testing cardiac pacers, and, more particularly, to a circuit for testing the sensitivity of a cardiac pacer.

2. Description of the prior art

Variations in the sensitivity of a heart pacer, particularly heart pacers of the so-called demand and synchronous types, have been recognized. In general, prior concerns have been expressed in heart pacer sensitivity variations with variations in the supply voltage. For example, if the supply voltage to an implanted cardiac pacer becomes too low to enable the pacer to properly sense R-waves, or other heart produced waveforms, to produce the desired result (i.e. inhibiting the pacer, synchronizing subsequent pulses, etc.), the pacer may be ineffective for its intended purpose.

Thus, pacers have been proposed which include means for varying the sensitivity of the pacer in known amounts for the purpose of determining the "capture margin" to produce an indication of the remaining pacer battery lifetime. This is done, for instance, in U.S. Pats. Nos. 3,837,348, and 3,857,085.

Insofar as is known to applicant, however, there is no apparatus which is suitable for directly measuring the sensitivity of the pacer to a particular voltage waveform. It is desirable, for example, to measure the sensitivity of a pacer under consideration to a waveform which varies with time as a function of the $sine^2$ of a 25 hertz signal.

SUMMARY OF THE INVENTION

In light of the above, it is, therefore, an object of the invention to present a circuit for measuring the sensitivity of a cardiac pacer.

It is another object of the invention to present a circuit for generating a voltage waveform of controllable amplitude which varies as a $sine^2$ function of a 25 hertz signal for measuring the sensitivity of a demand heart pacer.

These and other objects, features, and advantages will become apparent to those skilled in the art from the following detailed description when read in conjunction with the accompanying drawings and appended claims.

The invention, in its broad aspect, presents an analyzer for measuring the sensitivity of a cardiac pacer of the type which responds to a naturally produced heart signal. The analyzer includes means for applying signals to the pacer of controlled varying amplitude, and means for monitoring the response of the pacer to the applied signals. The analyzer includes additionally, means for monitoring the generation of the stimulation pulses of the pacer, and means for displaying the amplitude of the applied signals which just produces the desired response by said pacer.

In another aspect of the invention, a circuit is provided for generating the signal to be applied to the pacer which can be varied in a known manner as a $sine^2$ function of a signal of predetermined frequency.

BRIEF DESCRIPTION OF THE DRAWING

The invention as illustrated in the accompanying drawing wherein.

DETAILED DESCRIPTION OF THE PREFERRED EMBODIMENTS

Figure 1:
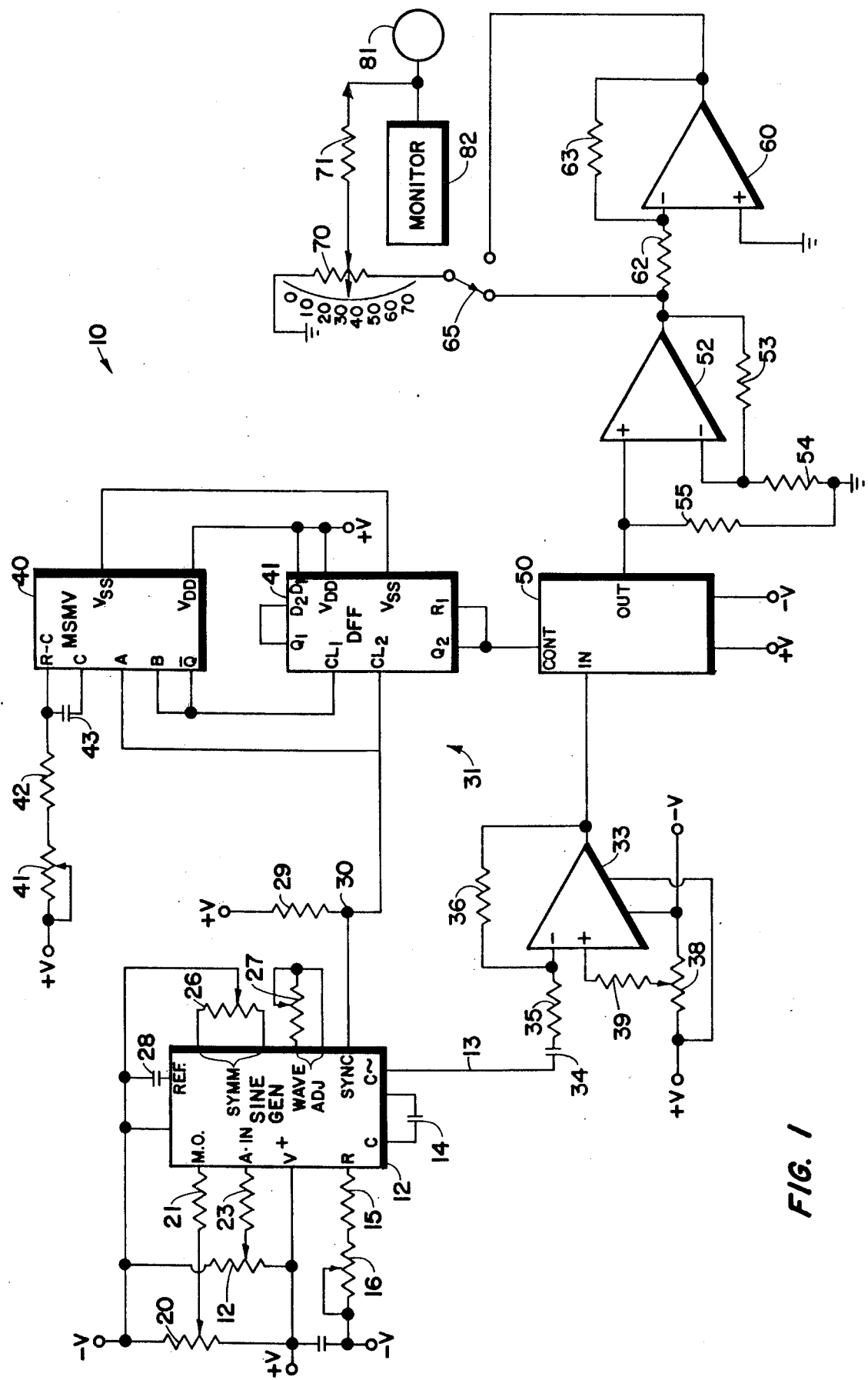
FIG. 1 illustrates a schematic diagram of a circuit for generating a signal having a voltage waveform which varies as a $sine^2$ function of a predetermined frequency, and which includes means for controllably varying the amplitude of said signal for application to a heart pacer the sensitivity of which is to be tested.

As shown in FIG. 1, a circuit 10 is presented which produces a signal which varies as a $sine^2$ function of a predetermined frequency for application to a heart pacer to determine the sensitivity thereof. The circuit 10 includes a function generator 12 which produces an output upon output line 13 which varies as a function of the sine of a signal at a controllable frequency. The function generator 12 includes a timing capacitor 14 and a fixed resistor 15 and variable resistor 16 which serve as the timing resistors. The frequency of the sine wave produced by the function generator 12 is controlled by the inverse of the product of the values of the capacitor 14 and the total of the resistors 15 and 16.

The function generator 12 additionally includes a variable resistor 20 connected between minus and positive terminals, the variable arm of which is connected by a series resistor 21 to the multiplier output of the function generator 12, in a manner well known in the art. Additionally, a variable resistor 22 is connected between the minus and plus voltage terminals, the variable arm of which is connected by a series resistor 23 to the amplitude input control terminal of the function generator 12. A variable resistor 26 is connected to the symmetry adjust terminals to enable the symmetry of the produced sine wave to be controlled. The variable arm thereof is connected to the negative terminal. Additionally, a variable resistor 27 is connected between the waveform adjusting terminals of the function generator 12 to control the shape of the produced sine wave. Finally, a reference bypass capacitor 28 is connected from the function generator 12 to the negative voltage terminal.

In addition to the sine wave produced on the line 13, sync pulses are produced on an output line 30 from the function generator 12. The sync pulses are at the frequency of the sine wave delivered to the output line 13, and are delivered to a control circuit 31, below described in detail.

The sine wave produced on the output line 13 is delivered to an inverting terminal of an operational amplifier 33 via a series capacitor 34. Two resistors 35 and 36 are provided to control the gain of the operational amplifier 33, in a well known manner, to produce a unity gain from input to output thereof. Additionally, a variable resistor 38 is connected between negative and positive terminals, the variable arm thereof being connected by a fixed resistor 39 to the non-inverting input of the operational amplifier 33 to control the offset voltage of the operational amplifier 33. In the embodiment illustrated, the offset voltage is set at ½ of the input signal.

The control circuit 31 includes a monostable multivibrator 40 and two D-type flip-flops 41. The frequency of the monostable multivibrator 40 is controlled by the value of the variable resistor 41 and the fixed resistor 42 and the capacitor 43. The monostable multivibrator is triggered by the leading edge of the sync pulse produced at the sync output of the function generator 12 upon the line 30 to produce an output upon the $\overline{Q}$ output line for a time controlled by the time constant of the aforementioned resistors 41 and 42 and capacitor 43.

The sync pulses produced upon the output line 30 are additionally connected to the clock input of the second D flip-flops of the D flip-flops 41. The output $\overline{Q}$ of the monostable multivibrator 40 is connected to the clock input of the first D flip-flop of the D flip-flop package 41.

As is apparent, the integrated circuit package presenting the D flip-flops 41 in the embodiment illustrated presents two D flip-flop circuits, (the various inputs and outputs are differentiated by the sub-scripts 1 and 2, respectively). The D input of the first flip-flop is connected to a high state or a positive voltage terminal, as shown. The output of the first D flip-flop at terminal $Q_1$ is connected to the input of the second D flip-flop at terminal $D_2$. The output of the second D flip-flop at terminal $Q_2$ is connected to the reset terminal of the first flip-flop at terminal $R_1$. The output of the second D flip-flop at terminal $Q_2$ is additionally controlled to the control terminal of a bilateral switch circuit 50. The output from the operational amplifier 33 is connected to the input of the bilateral switch circuit 50, and the output is connected to a buffer amplifier 52. The buffer amplifier 52 includes a feedback resistor 53 and a resistor 54 connected between the inverting input of the amplifier 52 to ground. A third resistor 55 is connected between the non-inverting input to the amplifier 52 and ground.

An inverter amplifer 60 is provided to present an output selectible regardless of the polarity of the signal produced. The gain of the inverter 60 is controlled by the resistors 62 and 63 to a unity value, the signal being applied from the output of the buffer amplifier 52 to the inverting input of the inverter circuit 60 as shown. The output of the inverter 60 is connected to one terminal of a polarity switch 65 and the output of the buffer amplifier 52 is connected to the other terminal thereof to enable the desired output polarity to be selected. The output from the circuit 10 as developed upon a variable resistor 70, and is delivered via a series resistor 71 to the output of the circuit.

The operation of the circuit 10 presently described is dependent upon the trigonometric function $\sin^2 = \frac{1}{2}(1-\cos 2\theta)$. The gain of the amplifier 33, as above described, is unity, and the sine function developed by the function generator 12 is applied to the inverting output thereof. The offset voltage, being adjusted, as above described, to ½ the voltage of the applied sine wave enables the operational amplifier to produce at its output the function ½ (1−Sin$\theta$). Since the trigonometric function above set forth provides that the angle in the cosine term is twice the angle in the desired sine$^2$ term (note that the sine$^2$ term is never directly produced) the frequency of the sine wave output upon the line 13 is chosen to be ½ of the desired angle. For instance, if the argument of the sine$^2$ term is to be 25 hertz, the frequency of the sine wave produced by the function generator 12 is adjusted to be 50 hertz.

The passage of the produced waveform at the output of the amplifier 33 is controlled through the bilateral switch by the sync pulses developed upon the line 30 from the function generator 12. By appropriately phasing the activation of the bilateral switch, the point at which the passage of the waveform from the amplifier 33 through the bilateral switch can be chosen. Therefore, by shifting the waveform ninety degrees, the output waveform produced at the output of the bilateral switch 50 can be ½(1−COS$\theta$ ) which, as above indicated, is the desired test pulse waveform equal to $\sin^2 (\theta/2)$. To achieve this, the sync pulses trigger the monostable multivibrator 40 for a total delay time controlled by the time constant of the resistors 41 and 42 and the capacitor 43, as above mentioned. Additionally, the sync pulses, being applied to the clock input of the second D flip-flop of the flip-flop package 41 produce the output upon the output terminal $Q_2$ equal to the D input at the time immediately prior to the sync pulse. However, until the $\overline{Q}$ output from the monostable multivibrator 40 changes from its low state during the time the monostable multivibrator 40 is triggered, the input to the second D flip-flop is zero or low. Therefore, the output upon the terminal $Q_2$ thereof, to control the bilateral switch 50, is low. When, thereafter, the monostable multivibrator 40 changes states after the predetermined delay time, the $\overline{Q}$ output thereof goes high, to produce a clock pulse to the first D flip-flop of the D flip-flop package 41. Thus, the output $Q_1$ will represent the high state of the D input of the first D flip-flop, which, in turn, is applied to the D input of the second flip-flop. Upon the reception of the next subsequent sync pulse upon the line 30, (which will be 90° displaced from the 0 position of the sine wave upon the line 13) the output $Q_2$ will go high, allowing the waveform from the amplifier 33 to pass therethrough. The waveform is then applied via the buffer 52 to the output of the circuit 10.

The output of the circuit 10, as above indicated, is connected to an input lead 80 of a cardiac pacer 81. The cardiac pacer 81, which may be of the demand, synchronous, or other type, responds to the waveform produced in a manner similar to that response produced by a naturally occurring heartwave. Thus, for example, in demand operation, if an electrical signal of sufficient magnitude is applied to the input of the pacer 81, its demand function will be inhibited. The inhibition of the pacer 81 can be monitored by a monitor circuit 82 in a well known manner.

Thus, the sensitivity of the pacer 81 can be determined by varying the variable resistor 70 to control the amplitude of the output pulses from the circuit 10 for application to the pacer 81 via the electrode 80. The resistor 70 is precalibrated to present an externally visually readable indication of the amplitude of the pulse generated in relation of the rotational position of the arm thereof, illustrated by the vertical numbers adjacent thereto . Thus, the sensitivity of the circuit can be read directly from the rotational position of the arm of the variable resistor 70 at the point at which the desired response from the pacer 81 (i.e. inhibition of a stimulation pulse) occurs.

The preferred embodiment of the pacer sensitivity measuring circuit 10 can be realized by the following component values, without limitation thereto.

Integrated Circuits

| Number | Type |
|---|---|
| 12 | XR-2206 (R . ohm) |
| 33, 52, 60 | MC 3403 (Motorola) |
| 50 | CD 4016 (RCA) |
| 41 | CD 4013 (RCA) |
| 40 | MC 14528 (Motorola) |

Resistors

| Number | Value |
|---|---|
| 20 | 25 kilohms (variable) |
| 22 | 100 kilohms (variable) |
| 16 | 2 megohms (variable) |

-continued

| Number | Value |
|---|---|
| 21 | 51 kilohms |
| 23 | 30 kilohms |
| 15 | 1 kilohm |
| 26 | 25 kilohms (variable) |
| 27 | 500 ohms (variable) |
| 29 | 10 kilohms |
| 35 | 20 kilohms |
| 36 | 20 kilohms |
| 39 | 20 kilohms |
| 38 | 100 kilohms |
| 41 | 1 megohm |
| 42 | 200 kilohms |
| 55 | 10 kilohms |
| 54 | 100 kilohms |
| 53 | 1 kilohm |
| 62 | 100 kilohms |
| 63 | 100 kilohms |
| 71 | 220 kilohms |
| 70 | 10 kilohms (variable) |

Capacitors

| Number | Value |
|---|---|
| 14 | 0.1 microfarads |
| 29 | 1 microfarad |
| 34 | 4.7 microfarads |
| 43 | .1 microfarads |

Although the invention has been described and illustrated with a certain degree of particularity, it is understood that the present disclosure has been made only by way of example and that numerous changes in details of construction and the combination and arrangement of parts may be resorted to without departing from the spirit and scope of the invention as hereinafter claimed.

I claim:

1. An analyzer for measuring the sensitivity of a cardiac pacer of the type which responds to a heart generated signal, comprising:

means for applying signals to said pacer of controlled varying amplitude, means for monitoring the response of said pacer to said applied signals, means for monitoring the generation of stimulation pulses of said pacer, and means for displaying the amplitude of the signals which just produced the response of said pacer.

2. The analyzer of claim 1 wherein said displaying means displays the amplitude of the voltage which inhibits said pacer from producing stimulation pulses.

3. A circuit for measuring the sensitivity of a cardiac pacer to electrical signals comprising:

a generator for producing a voltage waveform which varies as a $sine^2$ function, means for applying said voltage waveform to an input of said pacer, means for measurably varying the amplitude of said waveform, means for monitoring an output of said pacer, whereby the response to said pacer to said waveform can be observed, and means for displaying the amplitude of said voltage waveform which inhibits the output of said pacer.

4. The circuit of claim 3 wherein said displaying means displays a numerical representation of said amplitude of said voltage waveform.

5. The circuit of claim 3 wherein said generator for producing a voltage waveform produces pulses, each having a voltage waveform described by $\frac{1}{2}(1-COS2\theta)$.

* * * * *